United States Patent [19]

Kilburn et al.

[11] Patent Number: 5,137,819
[45] Date of Patent: Aug. 11, 1992

[54] CELLULOSE BINDING FUSION PROTEINS FOR IMMOBILIZATION AND PURIFICATION OF POLYPEPTIDES

[75] Inventors: Douglas G. Kilburn; Robert C. Miller; Richard A. J. Warren; Neil R. Gilkes, all of Vancouver, Canada

[73] Assignee: University of British Columbia, Vancouver, Canada

[21] Appl. No.: 216,794

[22] Filed: Jul. 8, 1988

[51] Int. Cl.$^5$ .................. C12N 11/12; C12N 15/00; C12P 21/00

[52] U.S. Cl. .................. 435/179; 435/69.1; 435/69.52; 435/69.7; 435/71.1; 435/172.3; 435/177; 435/195; 435/200; 435/209; 435/803; 935/11; 935/14

[58] Field of Search .................. 435/69.1, 69.52, 69.7, 435/71.1, 172.3, 177, 179, 803, 195, 200, 209; 935/11, 14; 514/2

[56] References Cited

U.S. PATENT DOCUMENTS 4,745,055 5/1988 Schenk et al. .................. 435/69.7 X

FOREIGN PATENT DOCUMENTS 0195680 9/1986 European Pat. Off. .......... 435/69.7
0244147A2 4/1987 European Pat. Off. .
0286239A1 3/1988 European Pat. Off. .

OTHER PUBLICATIONS

Warren et al., "A Bifunctional Exoglucanase-Endoglucanase Fusion Protein", *Gene* (1987) 61(3):421-427.
Bedouelle and Duplay, "Production in *Escherichia coli* and One-Step Purification of Bifunctional Hybrid Proteins Which Bind Maltose", *Eur. J. Biochem.* (1988) 171:541-549.
Greenwood et al., "Fusion to an Endoglucanase Allows Alkaline Phosphatase to Bind to Cellulose", *FEBS Letters* (1989) 244(1):127-131.
Ong et al., "Enzyme Immobilization Using the Cellulose-Binding Domain of a *Cellulomonas Fimi* Exoglucanase", *Bio/Technology* (1989) 7:604-607.
Halliwell and Griffin, "Affinity Chromatography of the Cellulase of Trichodermakoningii", *Biochem J.* (1978) 169:713-715.
Ghose and Bisaria, "Studies on the Mechanism of Enzymatic Hydrolysis of Cellulosic Substances", *Biotechnology and Bioengineering* (1979) 21:131-146.
Nummi et al., "Isolation of Cellulases by Means of Biospecific Sorption on Amorphous Cellulose", *Analytical Biochemistry* (1981) 116:137-141.
Whittle et al., "Molecular Cloning of a Cellulomonas Fimi Cellulase Gene in Escherichia Coli", *Gene* (1982) 17:139-145.
Zoller and Smith, "Oligonucleotide-Directed Mutagenesis Using M13-Derived Vectors: an Efficient and General Procedure for the Production of Point Mutations in Any Fragment of DNA", *Nuc. Acids Res.* (1982) 10:6487-6501.
Vieira and Messing, "The pUC Plasmids, an M13mp7-Derived System for Insertion Mutagenesis and Sequencing with Synthetic Universal Primers", *Gene* (1982) 19:259-268.
Ooshima et al., "Adsorption of Cellulase from Trichoderma Viride on Cellulose", *Biotechnology and Bioengineering* (1983) 25:3103-3114.
Remaut et al., "Improved Plasmid Vectors with a Thermoinducible Expression and Temperature-Regulated Runaway Replication", *Gene* (1983) 22:103-113.

(List continued on next page.)

*Primary Examiner*—David M. Naff
*Attorney, Agent, or Firm*—Barbara Rae-Venter

[57] ABSTRACT

A fusion protein is prepared containing a polypeptide such as an enzyme and an amino acid sequence having a substrate binding region of a polysaccharidase such as cellulase that has essentially no polysaccharidase activity. By contacting the fusion protein with an affinity matrix containing a substrate such as cellulose for the cellulase substrate binding region, the substrate binding region binds to the affinity matrix to immobilize the polypeptide. The polypeptide can be purified by separating the fusion protein or polypeptide from the affinity matrix.

7 Claims, 8 Drawing Sheets

OTHER PUBLICATIONS

Zoller and Smith, "Oligonucleotide-Directed Mutagenesis of DNA Fragments Cloned Into M13 Vectors", *Methods in Enzymology* (1983) 100:468-501.

Moloney and Coughlan, "Sorption of Talaromyces Emersonii Cellulase on Cellulosic Substrates", *Biotechnology and Bioengineering* (1983) 25:271-280.

Gilkes et al., "A Mutant of Escherichia Coli That Leaks Cellulase Activity Encoded by Cloned Cellulase Genes From Cellulomonas Fimi", *Bio/Technology* (1984).

Langsford et al., "The Cellulase System of Cellulomonas Fimi", *Journal of General Microbiology* (1984) 130:1367-1376.

Ryu et al., "Competitive Adsorption of Cellulase Components and Its Signifigance in a Synergistic Mechanism", *Biotechnology and Bioengineering* (1984) 26:488-496.

Gilkes et al., "Mode of Action and Substrate Specificities of Cellulases From Cloned Bacterial Genes", *The Journal of Biological Chemistry* (1984) 259 (16):10455-10459.

Gilkes et al., "Isolation and Characterization of Escherichia Coli Clones Expressing Cellulase Genes From Cellulomonas Fimi", *Journal of Microbiology* (1984) 130:1377-1384.

Yanisch-Perron et al., "Improved M13 Phage Cloning Vectors and Host Strains: Nucleotide Sequences of the M13mp18 and pUC19 Vectors", *Gene* (1985) 33:103-119.

Wong et al., "Characterization and Structure of an Endoglucanase Gene cenA of Cellulomonas Fimi", *Gene* (1986) 44:315-324.

Van Tilbeurgh et al., "Limited Proteolysis of the Cellobiohydrolase I from Trichoderma Ressei: Separation of Functional Domains", *FEBS Letters* (1986) 204(2):223-227.

Warren et al., "Sequence Conservation and Region Shuffling in an Endoglucanase and an Exoglucanase From Cellulomonas Fimi", *Proteins:Structure, Function and Genetics* (1986) 1:335-341.

O'Neill et al., "Structure of the Gene Encoding the Exoglucanase of Cellulomonas Fimi", *Gene* (1986) 44:325-330.

Williamson and Stutzenberger, "Adsorption of Thermomonospora Curvata Cellulases on Insoluble Substrates", *Letters in Applied Microbiology* (1987) 5:101-105.

Boyer et al.; "Fractionation of Aspergillus Niger Cellulases by Combined Ion Exchange Affinity Chromatography", *Biotechnology and Bioengineering* (1987) 29:176-179.

Langsford et al., "Glycosylation of Bacterial Cellulases Prevents Proteolytic Cleavage Between Functional Domains", *FEBS Letters* (1987) 225(1,2):163-167.

Teeri et al., "Homologous Domains in Trichoderman Reesei Cellulolytic Enzymes: Gene Sequence and Expression of Cellobiohydrolase II", *Gene* (1987) 51:43-52.

Gutierrez et al., "The Use of Transposon TnphoA to Detect Genes for Cell Envelope Proteins Subject to a Common Regulatory Stimulus", *J. Mol. Biol.* (1987) 195:289-297.

Tomme et al., "Studies of the Cellulolytic System of Trichoderma Reesei QM 9414 Analysis of Domain Function in Two Cellobiohydrolases by Limited Proteolysis", Eur. J. Biochem (1988) 170:575-581.

Omolabi et al., Applied and Environmental Microbiology, vol. 54, No. 2, Feb. 1988, pp. 518-523.

FIG. 1

| Plasmid | Promoter | R.B.S. | Sequence of the Exg or Exg-BGal fusion | Exg activity[3] |
|---|---|---|---|---|
| pUC12-1.1cex | lac | cex | -41  -39  -37  -35          -3 -2 -1 +1 +2<br>M P R T T P A         A Q A A T<br>ATGCCTAGGACCACGCCCGCA...GCCCAGGCCGCGACC...... | 1.0 |
| pUC12-1.1(737) | lac | lacZ | T M I T N S  s  s  p  g  (-40) P  R<br>ATGACCATGATTACGAATTCGAGCTCGCCCGGGGATCCTAGG....<br>BamHI StyI | 150 |
| pUC12-1.1(PTIS) | lac | PTIS | (-40)<br>M D P R T<br>TGGAGGAAAAAATT ATGGATCCTAGGACC........<br>BamHI StyI | 146 |

A. SCHEMATIC DIAGRAM FOR FED-BATCH PRODUCTION, PURIFICATION, AND IMMOBILIZATION OF THE FUSION ENZYME. ▨ = AVICEL ALONE; ▦ =AVICEL + SBD-β GLUCOSIDASE; ▨ =MEDIUM + CELLS.

FIG. 7

B. SCHEMATIC OF A REUSABLE FERMENTOR-IMMOBILIZATION COLUMN SET-UP FOR THE HYDROLYSIS OF CELLULOSIC MATERIALS TO GLUCOSE.

CELLULOSE BINDING FUSION PROTEINS FOR IMMOBILIZATION AND PURIFICATION OF POLYPEPTIDES

INTRODUCTION

1. Technical Field

This invention relates to novel polypeptide compositions, including chimeric polypeptides capable of binding to a polysaccharide matrix, and methods for their preparation using recombinant DNA techniques.

2. Background

Production of foreign proteins by expression in microbial systems may become a significant source of high value, medically important proteins. Purification and recovery of recombinant proteins are major considerations in the design of a fermentation process. While traditional means of protein purification can be used to isolate a product, improved means include the use of fusion proteins. Fusion proteins can be purified by affinity chromatography, the desired component of the fusion protein being purified by virtue of its covalent attachment to a polypeptide which binds to an affinity matrix. As an example, fusion proteins comprising a polypeptide of interest fused to β-galactosidase be purified using a p-amino-phenyl-β-D-thiogalactoside-Sepharose column. Such a method has been used for purification of immunogenic polypeptides such as viral antigens. Staphylococcal protein A can also be used for affinity purification of fusion proteins by virtue of its specific binding to the Fc portion of immunoglobulins.

In addition to purification, recovery of the original components from the fusion is often desirable. Both biochemical and biological methods have been devised to cleave fusion proteins into their component polypeptides or segments. Introduction of acid-labile aspartyl-proline linkages between the two segments of a fusion protein facilitates their separation at low pH. The major requirement of this system is that the desired segment of interest is not acid-labile. Fusion proteins comprising hormones such as insulin and somatostatin have been cleaved with cyanogen bromide, which is specific for the carboxyl side of methionine residues to release the desired hormone. This method is not suitable when the desired protein contains methionine residues.

Cleavage of fusion proteins by site-specific proteolysis has also been investigated. Fusion proteins into which a chicken pro α-2 collagen linker was inserted could be specifically degraded by purified microbial collagenase to release the components of the fusion protein Other methods for purification and recovery of a desired recombinant protein include construction of a poly-arginine tail at the carboxyterminus of the protein. The arginine residues increase the overall basicity of the protein which facilitates purification of the desired protein by ion exchange chromatography. Subsequent removal of the poly-arginine tail by carboxypeptidase B regenerates the desired protein and allows purification from basic contaminants due to the reduction in pI of the desired protein.

It is of interest to develop a rapid and inexpensive method for purification or immobilization of a desired protein. Carbohydrate polymers such as cellulose are plentiful and inexpensive. Furthermore, a variety of enzymes bind specifically to carbohydrate polymers. It would therefore be of interest to prepare fusion proteins comprising at least the carbohydrate polymer-binding portion of such an enzyme as a means for immobilizing and/or purifying the fusion protein.

Relevant Literature

The affinity of cellulases for cellulose have been used for their purification (Boyer et al., *Biotechnol. Bioeng.* (1987) 29:176–179; Halliwell et al., *Biochem. J.* (1978) 169:713–735; Mart'yanov et al., *Biokhimiya* (1984) 19:405–104; Nummi et al., *Anal. Biochem.* (1981) 116:137–141; van Tilbeurgh et al., *FEBS Letters* (1986) 204:223–227). Several cellulase genes from *Cellulomonas fimi* have been cloned into *Escherichia coli* (Whittle et al., *Gene* (1982) 17:139–145; Gilkes et al., *J. Gen. Microbiol.* (1984) 130:1377–1384). Binding to Avicel (microcrystalline cellulose) has been used for purification of both native (Gilkes et al., *J. Biol. Chem.* (1984) 259:10455–10459) and recombinant enzymes (Owolabi et al., *Appl. Environ. Microbiol.* (1988) 54: 518–523). A bifunctional hybrid prtein which binds maltose has been described. Bedouelle et al., *Eur. J. Biochem.* (1988) 171:541–549.

Two of the *C. fimi* cellulases, an exoglucanases (Cex) and an endoglucanase (CenA), have been characterized and their genes, cex and cenA, have been sequenced (Wong et al., *Gene* (1986) 44:315–324; O'Neill et al., *Gene* (1986) 44:325–330). Predicted amino acid sequences show evidence of domain structure for these enzymes (Warren et al., *PROTEINS: Structure, Function, and Genetics* (1986) 1:335–341). Domain structures have also been observed in other cellulases (Teeri et al., *Publications* (1987) 38: Technical Research Centre of Finland; Teeri et al., *Gene* (1987) 51:43–52) and separation of domains by proteolytic cleavage has given some insight into domain function (Langsford et al., *FEBS Letters* (1987) 225: 163–167; Tomme et al., *Eur. J. Biochem.* (1988) 170:575–581; van Tilbeurgh et al., *FEBS Letters* (1986) 204:223–227). A serine protease found in C. fimi culture supernatants (Langsford et al., *J. Gen. Microbiol.* (1984) 130:1367–1376) has been shown to cleave substrate-bound recombinant CenA and Cex, releasing catalytically-active fragments with greatly reduced affinity for cellulose (Langsford et al., *FEBS Letters* (1987) 225:163–167). The remaining fragments correspond to the irregular regions of low charge density in both enzymes and are believed to constitute the cellulose-binding domains of the enzymes.

SUMMARY OF THE INVENTION

Methods and compositions are provided for preparing a fusion protein capable of binding to a polysaccharide matrix. The fusion protein comprises at least the substrate binding region of a polysaccharidase. The fusion protein is prepared by transforming into a host cell a DNA construct comprising a fragment of DNA encoding at least the substrate binding region of a polysaccharidase gene ligated to a gene encoding a polypeptide of interest and growing the host cell to express the fused gene. The resulting fusion protein readily binds to a solid support comprising a substrate for the polysaccharidase. The composition can be used to prepare a polysaccharide matrix comprising any of a variety of polypeptides of interest or in a method for purifying either the fusion protein or the polypeptide of interest.

BRIEF DESCRIPTION OF THE DRAWINGS

FIG. 5-1 and 5-2 show construction of pE01. Sp=SphI; Ss=hybrid SmaI; Sa=SalI; PS=PstI; ABG=β-galactosidase gene Cex exogluconase gene; SBD=substrate binding domain; PT=proline-threonine box hatched box multiple cloning site.

DESCRIPTION OF THE SPECIFIC EMBODIMENTS

Novel compositions comprising fusion proteins in which at least the substrate binding portion of a cellulase is fused to a protein of interest, as well as methods for their preparation, are provided. The compositions may be prepared by transforming into a host cell a CNA construct comprising at least a fragment of DNA encoding the substrate binding region of a polysaccharidase gene ligated to a DNA sequence encoding the peptide of interest and growing the host cell to express the fused gene. The host cell may be either a eukaryotic or a prokaryotic cell. The fusion proteins provide for a wide variety of applications including purification of the protein of interest, immobilization of the protein of interest, and preparation of solid phase diagnostics, as well as any other applications where a means of binding a compound of interest to a polysaccharide matrix is desired.

Novel polypeptide compositions will for the most part have the following formula:

SBR—MR—X wherein:
SBR can be either the N-terminal or the C-terminal region of the subject polypeptide and is characterized as having from 108 to 134 amino acids which correspond to a consecutive sequence of amino acids from at least the substrate binding region of a polysaccharidase;

MR is the middle region, and may be a bond; short linking group of from 2 to 30 carbon atoms, or have from about 2 to about 20 amino acids. The region may include an amino acid sequence providing for specific cleavage of the fusion protein, usually a sequence corresponding to that recognized by a proteolytic enzyme of high specificities such as an IgA$_1$ protease; and X can be either the N-terminal or the C-terminal region and may be any peptide of interest. It is characterized as having up to the entire sequence of a polypeptide of interest, or a fragment thereof, and may be an enzyme, a hormone, an immunoglobulin, a dye, etc.

Preparation of Fusion Proteins

The techniques used in isolating a cellulase gene are known in the art, including synthesis, isolation from genomic DNA, preparation from cDNA, or combinations thereof. The various techniques for manipulation of the genes are well known, and include restriction, digestion, resection, ligation, in vitro mutagenesis, primer repair, employing linkers and adapters, and the like (see Maniatis et al., *Molecular Cloning*, Cold Spring Harbor Laboratory, Cold Spring Harbor, New York, 1982).

Generally, the method comprises preparing a genomic library from an organism expressing a cellulase with the desired characteristics. Examples of such cellulases are those obtainable from strains belonging to the species of *Cellulomonas fimi, Trichoderma reesei*, and the like. The genome of the donor microorganism is isolated and cleaved by an appropriate restriction enzyme, such as BamHI. The fragments obtained are joined to a vector molecule which has previously been cleaved by a compatible restriction enzyme. An example of a suitable vector is plasmid pBR322 which can be cleaved by the restriction endonuclease BamHI. The amino acid sequence of a cellulase can be used to design a probe to screen a cDNA or a genomic library prepared from mRNA or DNA from cells of interest as donor cells for a cellulase gene.

By using the cellulase cDNA or a fragment thereof as a hybridization probe, structurally related genes found in other microorganisms can be easily cloned. Particularly contemplated is the isolation of genes from organisms that express cellulase activity using oligonucleotide probes based on the nucleotide sequences of cellulase genes obtainable from *Cellulomonas fimi*. Such probes can be considerably shorter than the entire sequence but should be at least 10, preferably at least 14, nucleotides in length. Longer oligonucleotides are also useful, up to the full length of the gene, preferably no more than 500, more preferably no more than 250, nucleotides in length. Both RNA and DNA probes can be used.

In use, the probes are typically labeled in a detectable manner (for example with $^{32}P$, $^3H$, biotin or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known to those skilled in the art.

Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

In order to isolate the cellulose-binding domain of the cellulase, several genetic approaches may be used. One method uses restriction enzymes to remove a portion of the gene and then to fuse the remaining gene-vector fragment in frame to obtain a mutated gene that encodes a protein truncated for a particular gene fragment. Another method involves the use of exonucleases such as Bal31 to systematically delete nucleotides either externally from the 5' and the 3' ends of the DNA or internally from a restricted gap within the gene. These gene deletion methods result in a mutated gene encoding a shortened protein molecule which may then be evaluated for substrate binding ability. Appropriate substates for evaluating and binding activity include Avicel, cotton fibres, filter paper, Kraft or ground wood pulp, and the like.

Once a nucleotide sequence encoding the substrate binding region has been identified, either as cDNA or chromosomal DNA, it may then be manipulated in a variety of ways to fuse it to a DNA sequence encoding a polypeptide of interest. The polysaccharide binding encoding fragment and the DNA encoding the polypeptide of interest are then ligated. The resulting ligated DNA may then be manipulated in a variety of ways to provide for expression. Microbial hosts may be employed which may include, for example bacteria such as *E. coli,* and eukaryotes such as *Saccharomyces cerevisiae.*

Preparation of plasmids capable of expressing fusion proteins having the amino acid sequences derived from fragments of more than one polypeptide with sequence changes when necessary to introduce a convenient restriction site are described in detail in the experimental section.

Illustrative transcriptional regulatory regions or promoters include, for bacteria, the lac promoter, the TAC promoter, lambda left and right promoters, trp and lac promoters, tac promoter, and the like. The transcriptional regulatory region may additionally include regulatory sequences which allow the time of expression of the fused gene to be modulated, for example the presence or absence of nutrients or expression products in the growth medium, temperature, etc. For example, expression of the fused gene may be regulated by temperature using a regulatory sequence comprising the bacteriophage lambda PL promoter, the bacteriophage lambda OL operator and a temperature-sensitive repressor. Regulation of the promoter is achieved through interaction between the repressor and the operator.

The expression cassette may be included within a replication system for episomal maintenance in an appropriate cellular host or may be provided without a replication system, where it may become integrated into the host genome. The DNA may be introduced into the host in accordance with known techniques, such as transformation, using calcium phosphate-precipitated DNA, transfection by contacting the cells with a virus, microinjection of the DNA into cells or the like.

Once the fused gene has been introduced into the appropriate host, the host may be grown to express the fused gene. In some instances, it may be desirable to provide for a signal sequence (secretory leader) upstream from and in reading frame with the structural gene, which provides for secretion of the fused gene. Illustrative secretory leaders include the secretory leaders of penicillinase, immunoglobulins, T-cell receptors, outer membrane proteins, and the like. By fusion in proper reading frame the chimeric polypeptide may be secreted into the medium.

Where the product is retained in the host cell, the cells are harvested, lysed and the product isolated and purified by binding to a polysaccharide substrate. Where the product is secreted, the nutrient medium may be collected and the product isolated by binding to a polysaccharide matrix. To produce an active protein it may be necessary to allow the protein to refold.

The recombinant products may be glycosylated or non-glycosylated, having the wild-type or other glycosylation. The amount of glycosylation will depend in part upon the sequence of the particular peptide, as well as the organism in which it is produced. Thus expression of the product in *E. coli* cells will result in an unglycosylated product, and expression of the product in insect cells generally will result in less glycosylation than expression of the product in mammalian cells. Expression in yeast may result in hyperglycosylation.

In addition to producing fusion proteins from fused genes, the fusion protein could be made chemically. The substrate binding region or multiples thereof is produced on its own, purified and then chemically linked to the polypeptide of interest using techniques known to those skilled in the art.

Use of Fusion Proteins

The subject compositions find a wide variety of applications. Thus the subject compositions can be used in which recombinant proteins are fused to the polysaccharide binding region of the cellulase for a generalized protein purification technique. The recombinant protein can be readily cleaved from the polysaccharide binding region by the use of a protease specific for a sequence present in the cellulose binding region. Examples of biologicals which can be purified in this way include interleukin 2, Factor VIII, ligninase, TPA.

The subject compositions can also be used as a means of immobilizing a polypeptide of interest on a cellulosic support, since the substrate binding region adsorption to cellulose is strong and specific. The immobilized systems may find a number of uses, including use in preparing solid state reagents for diagnostic assays, the reagents including enzymes, antibody fragments, peptide hormones, etc.; drug binding to decrease clearance rate where the cellulose may be either soluble, for example carboxymethyl cellulose or a solid support such as a microcrystalline cellulose (Avicel) where the drug is a polypeptide such as interleukin 2; drug delivery, for example bound to carboxymethyl cellulose and may be used in conjunction with binding of an adjuvant to the same cellulose support for example for enhancement of immunospecificity of the drug to be delivered; dye binding, for example coupling of paints or dyes to cellulosic surfaces; printing on for example paper and cloth (cotton); and to provide hydrolysis or synergy, for example targeting of enzymes such as ligninase for treatment of wood chips, targeting of porphyrins, for example for bleaching of wood pulp; agricultural uses such as binding of insecticides to plant surfaces, for example BT toxin or other antimicrobials; for nitrogen fixation, for example for binding of organisms to root surfaces; sustained fertilizer release; and sustained release of fungicides; they may also be used under conditions of high salt such as in a marine environment for anti-fouling of surfaces exposed to sea water where transfer to fresh water will remove the fusion protein.

Depending upon the particular protocol and the purpose of the reagent, the polypeptide may be labeled or unlabeled. A wide variety of labels have been used which provide for, directly or indirectly, a detectable signal. These labels include radionuclids, enzymes, fluoresors, particles, chemiluminesors, enzyme substrates or co-factors, enzyme inhibitors, magnetic particles, etc.

A wide variety of methods exist for linking the labels to the polypeptides, which may involve use of the end terminal amino group for functionalization to form a pyrolezone, while other free amino groups are protected, where the pyrolezone may then be contacted with various reagents, for example amino groups, to link to the detectable signal generating moiety.

The following examples are offered by way of illustration and not by way of limitation.

EXPERIMENTAL

Abbreviations. pNPC=p-nitrophenyl-$\beta$-D-cellobioside; HPA=hide powder azure; gCenA and gCex=the glycosylated forms of CenA and Cex from *C. fimi;* ngCenA and ngCex=the non-glycosylated forms of CenA and Cex from recombinant *E. coli;* RPC=reverse-phase chromatography; SDS-PAGE=sodium dodecyl sulfate-polyacrylamide gel electrophoresis; $\alpha$-Pro/Thr=rabbit antiserum directed against synthetic Cex Pro/Thr box; PMSF=phenylmethylsulfonyl fluoride.

Biological Culture Deposits. A derivative of the cloned gene CenA on plasmid pGEC-2 in Escherichia coli C600 was deposited on Apr. 23, 1986 with the American Type Culture Collection (ATCC), 12301 Park Lawn Drive, Rockville, Md., 20852, and given ATCC Accession No. 67101. A derivative of the cloned gene Cex on plasmid pEC-1 was deposited on May 29, 1986 and given ATCC Accession No. 67120. *E. coli* JM83, pUC12-1.1 cex was deposited on Apr. 23, 1986, and given ATCC excession No. 67102.

EXAMPLE 1

Construction of Cex Expression Plasmids

A. Bacterial Strains and Plasmids

The host strain C600 (thr-1 leu-6 thi-1 supE44 lacyYl tonA21) and the plasmids pcI857 and pCP3 were obtained from Erik Remaut and are described in Gene (1983) 22:103–113.

B. Recombinant DNA Techniques

DNA preparations and enzyme reactions were performed as described by Maniatis et al., *Molecular Cloning: A Laboratory Manual,* Cold Spring Harbor Laboratory, Cold Spring Harbor, NY. Restriction endonucleases, DNA polymerase I (Klenow fragment), T4 DNA ligase, and the portable translation initiation site (PTIS) were purchased from Pharmacia Inc. Bacterial transformations of plasmids containing the leftward promoter ($p_L$) of bacteriophage lambda into strains carrying the cI857 gene of phage lambda were carried out by the method of Maniatis et al., supra, 1 except for the following modification. The bacterial cells were heat shocked at 34° C. for 2 min, incubated in LB medium for 1 hr, and then plated on selective medium.

C. Growth and Induction of Bacteria

Bacteria were grown in LB (Maniatis, supra) medium with the addition after autoclaving of 0.4% glucose, 50 $\mu$g of kanamycin per ml, and 75 $\mu$g of ampicillin per ml. After growth at 30° C. to an optical density at 600 nm of 0.3, the cultures were divided, and at 41° C. (induced).

D. Isolation of the cex Gene

The cex gene from C. fimi was isolated as described in U.S. patent application Ser. No. 06/859,042, filed May 2, 1986, now abandoned in favor of continuing application Ser. No. 874,292, filed Jun. 6, 1986, now abandoned, and continuing application Ser. No. 630,558, filed Dec. 18, 1990, which disclosure is incorporated herein by reference.

E. Plasmid Constructions 1. pUC12-1.1cex.

Figure 1:
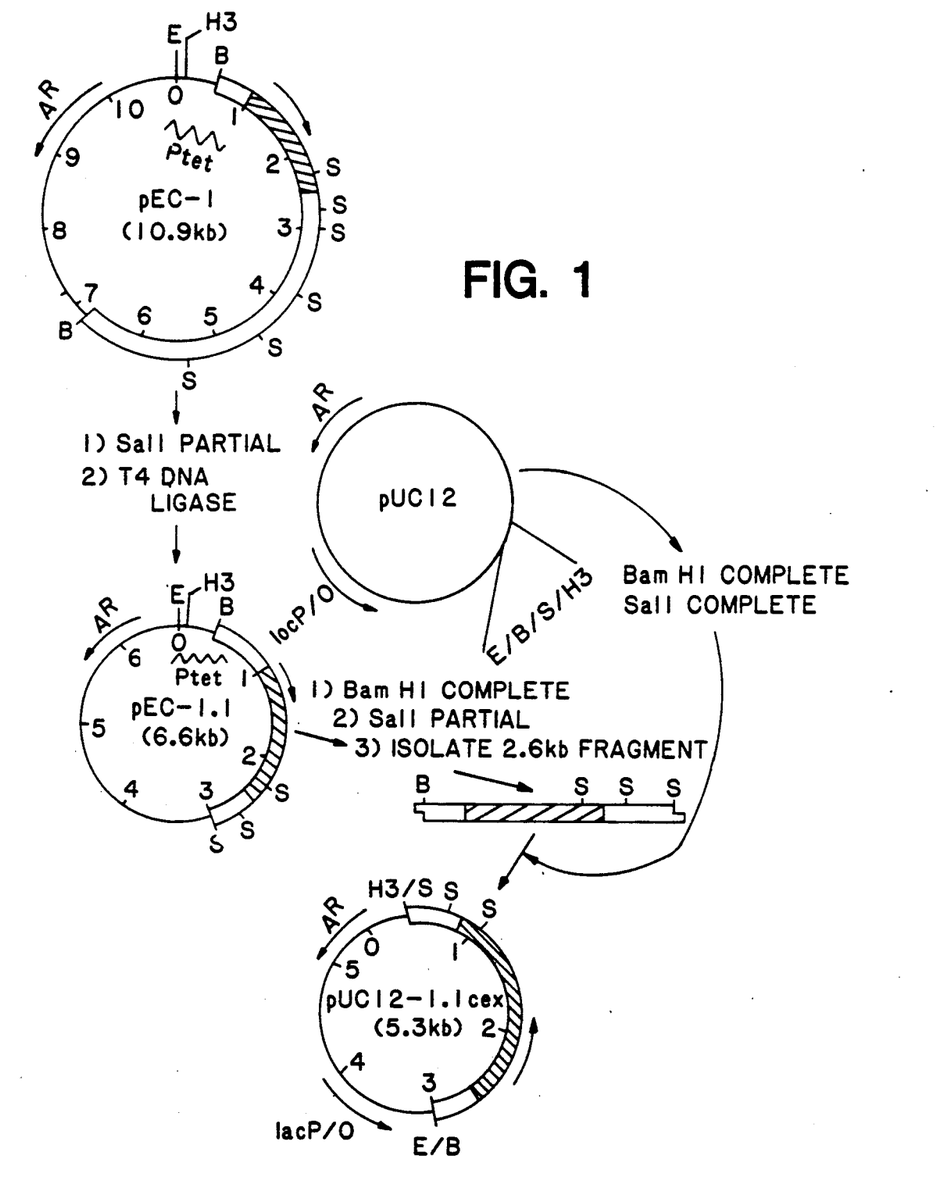
FIG. 1 shows construction of Cex-expressing plasmids pEC-1.1, and pUC12-1.1cex. The functional orientations of the gene coding for β-lactamase (Ap$^r$), Cex (a cross hatch square) and the promoters for lac are indicated by arrows. Restriction sites: B=BamHI; E=EcoRI; H3=HindIII; S=SalI.

The cex gene was cloned on a 6.6-kilobase-pair (kbp) BamHI fragment of C. fimi DNA ligated into the BamHI site of pBR322, giving pEC-1 (FIG. 1). The cex gene was localized by deletion analysis to a 2.56-kbp BamHI-SalI DNA fragment yielding pEC-1.1 (FIG. 1). The plasmid pUC12-1.1cex (FIG. 1) contains the 2.56-kbp fragment from pEC-1.1 positioned in opposite orientations downstream from the promoter-operator region of the *E. coli* lactose operon (lacZp/o) in the plasmid pUC12 (Gene (1982) 19:259–268). The plasmid pEC-1, was described by Whittle et al., Gene (1982) 17:139–145 and Gilkes et al., *J. Gen. Microbiol.* (1984) 130:1377–1384, which disclosures are incorporated herein by reference. The DNA sequence for the RBS, translational initiation site, and amino terminus of fusion junctions of $\beta$Gal-Exg expression plasmid pUC12-1.1cex are shown below in Table 1.

2. pUC12-1.1(737).

Figure 2:
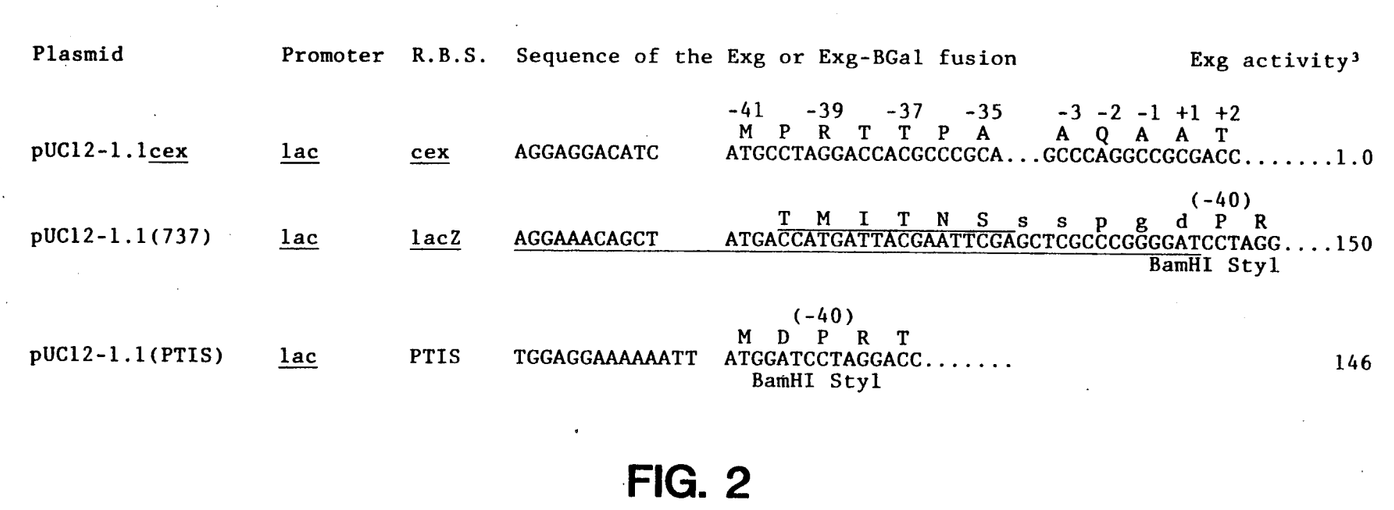
FIG. 2 shows obtaining pUC12-1.1(PTIS).

For the construction of pUC12-1.1(737), the 5' untranslated sequences, the ribosome binding site (RBS), and the initiating codon of the cex gene were first removed and replaced with the promoter operator region, the RBS, and the amino terminus of ($\beta$Gal) from the *E. coli* lac operon and then with the RBS-ATG sequences of the PTIS. In the first step, pUC12-1.1cex was cut with StyI and BamHI, the staggered ends were repaired with DNA polymerase I (Klenow fragment), and the plasmid DNA was ligated under dilute conditions to give pUC12-1.1(737). This manipulation results in (i) the in-frame fusion between codon 2 of the Cex leader sequence and codon 11 of the alpha-fragment of $\beta$Gal encoded by pUC12; (ii) the regeneration of the StyI cleavage site; and (iii) the replacement of the cex initiating codon with a BamHI cleavage site. The nucleotide sequence and deduced amino acid sequence of the $\beta$Gal-Cex fusion region of pUC12-1.1(737) are shown in FIG. 2.

3. pUC12-1.1(PTIS).

To obtain pUC12-1.1(PTIS), pUC12-1.1(737) was cut with EcoRI and BamHI, and the 17-bp PTIS with an EcoRI and a BamHI cohesive end was inserted. This procedure resulted in the in-frame fusion of the second codon of the cex leader sequence to the initiator ATG of the PTIS. (See FIG. 2)

PTIS

AATTTGGAAAAATTATG
ACCTTTTTAATACCTAG

DNA sequences of the RBS, translational initiation site, and amino terminus of fusion junctions of $\beta$Gal-Exg expression plasmids. pUC12-1.1cex codes for unfused cex gene products. The numbering of the codons of the natural cex gene product in pUC12-1.1cex begins with the initiating ATG of the leader sequences as −41 and the first codon of the mature Exg as +1. The first cex codon in the $\beta$Gal-Exg fusions retains its original position number. The deduced amino acid sequence is shown in single-letter code over the DNA sequence. The nucleotides and amino acids derived from $\beta$Gal are underlined. Lower-case amino acids are of non-lac origin and are derived from the linker region in pUC12. The restriction sites StyI, AvaII, and EcoRII in the amino terminus of the cex gene were used for fusion of the cex gene to the amino terminus of $\beta$Gal in pUC12.

A Exg activity is expressed as nanomoles of p-nitrophenyl released per minute per milligram of total cell protein.

EXAMPLE 2

Construction of CenA Expression Plasmids

A. Bacteria and Medium

*E. coli* JM101 was used for all cenA experiments. All cultures were grown on LB medium, solidified with 1.5% (w/v) agar when necessary. Ampicillin was added at a final concentration of 100 μg/ml. CenA activity was detected by staining with Congo red after growth of colonies on LB containing 1.0% (w/v) agar and 1.0% (w/v) carboxymethyl cellulose (CMC). Liquid cultures were 10 or 50 ml in 50 or 250 ml Erlenmyer flasks; they were grown in a New Brunswick Gyrotory water bath at 200 rpm.

B. DNA Techniques

Plasmids were released from *E. coli* by alkaline lysis and purified by centrifugation to equiliubrium in CsCl-ethidium bromide gradients. Digestion with restriction endonucleases, ligation of fragments and transformation of *E. coli* were performed as described.

C. Other Methods

Extracts were prepared by rupturing the cells with a French press. Enzymes were released from the periplasm by osmotic shock. Culture supernatants were obtained by centrifugation. All enzymes were assayed at 30° C. Endoglucanase from *E. coli* JM101/pUC18-1.6 cenA was purified by immunoadsorbent chromatography, followed by anion exchange chromatography on Mono Q resin with a gradient of 0–1.0 M NaCl in 20 mM piperazine, pH 9.8. Amino acid sequencing was by automated Edman degradation using an Applied Biosystems 470A gas-phase sequenator.

D. Isolation of the CenA Gene

The CenA gene from C. fimi was isolated a described in U.S. patent application Ser. No. 894,326, filed Aug. 7, 1986, now abandoned in favor of continuing application Ser. No. 630,396, filed Dec. 18, 1990.

E. Plasmid Construction

Figure 4A:
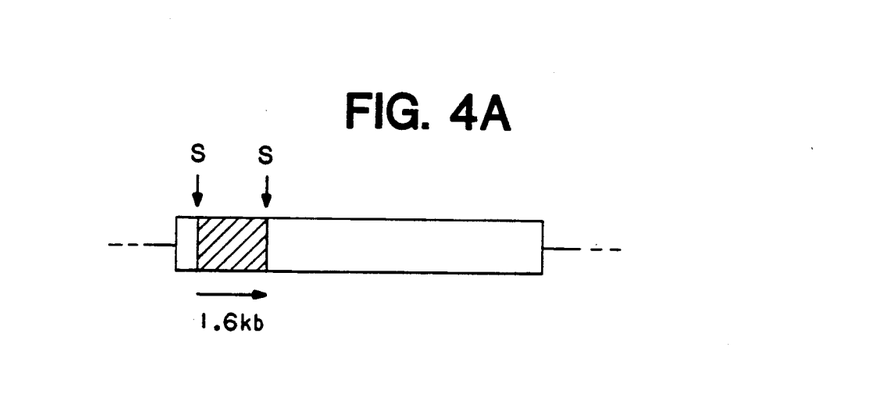
FIGS. 4A and 4B show plasmid construction for obtaining pUCEC2.
Figure 4B:
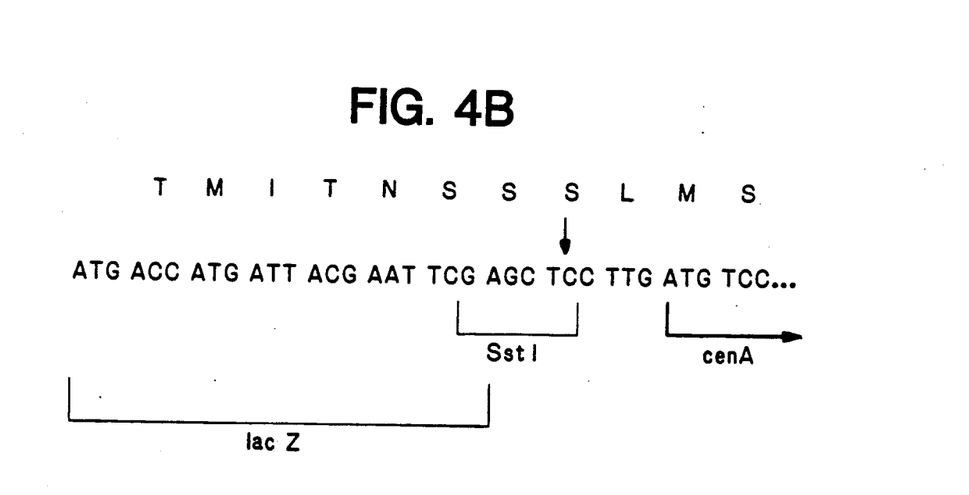

A 1.6-kb SstI fragment from the 6.0-kb insert of C. fimi DNA in pcEC2 was purified and sub-cloned into the SstI site of pUC18 to form pUCEC2, a schematic representation of which is shown in FIGS. 4A and 4B. The line represents pBR322 DNA; the box is C. fimi DNA; the hatched area is the cenA coding sequence; the arrow, shows the direction of transcription; S is SstI; FIG. 4A pcEC2; (FIG. 4B) the nucleotide and amino acid sequences at the fusion point of lacZ and cenA in pUCEC2.

EXAMPLE 3

Construction of Expression Cassette Containing Fusion of cex SBD Gene Fragment and Agrobacterium β-glucosidase Gene abg) and Characterization of Fusion Protein A. Construction of Expression Cassette Plasmid pUC12-1.1cex (PTIS) is cut to completion with PstI. Since both the vector and the insert have each a PstI restriction site, two possible fragments are formed. The smaller fragment (approximately 1071 bp) is isolated. This DNA fragment corresponds to that portion beginning from the PstI site of the insert at nt 1515 to the PstI site of the vector. This PstI-PstI fragment is then completely digested with SphI to produce three fragments (55 bp, 72 bp and 944 bp). The largest SphI-PstI fragment is isolated.

Figure 3:
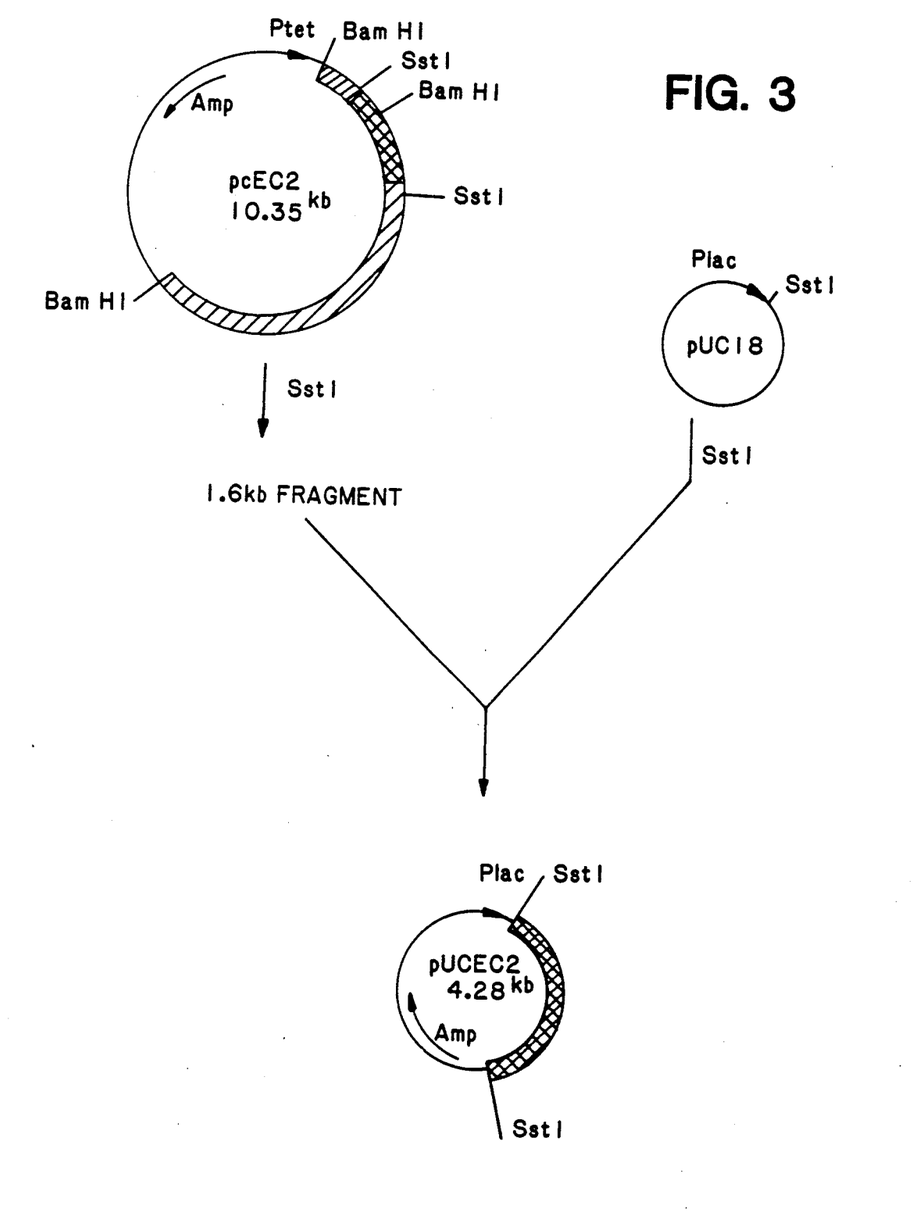
FIG. 3 shows construction of pUCEC.2.

The larger abg gene fragment (PstI-SphI) and the smaller cex SBD fragment (SphI-PstI) (see FIG. 3) are ligated together in-frame to obtain the desired plasmid construct (approximately 4954 bp). This construct is called pE01. Plasmid pE01 corresponds to a vector which is 2700 bp and the fused cex SBD-abg insert which is 2254 bp. The plasmid construct is transformed into *E. coli* JM101.

B. Enzymactic and PAGE Characterization of the Fusion Protein

The fusion protein encoded by pE01 is characterized for its catalytic activity compared to the original Abg. and for its ability to bind to Avicel compared to the original Cex. Characterization of catalytic activity includes determination of the kinetic properties (e.g., $K_m$ and $V_{max}$) and substrate specificity of the fusion enzyme. Enzyme activity is determined by the amount of glucose produced from a fixed concentration of cellobiose under standard assay time, temperature, pH, ionic strength and buffer. The glucose concentration is measured using a glucose analyzer (Beckman). The analysis is based on the initial rate of oxygen consumption in the conversion glucose to gluconic acid as determined by an oxygen electrode; the rate of oxygen consumption is directly proportional to the amount of glucose present relative to a known standard glucose solution.

The fusion protein is also analyzed by SDS-PAGE to determine relative molecular mass. The purified fusion protein can be cleaved with the protease from C. fimi to produce two or more other protein fragments. This is ascertained by running an SDS-PAGE of a proteolytic cleavage mixture of the fusion protein and doing a zymogram using a fluorescent glucoside derivative, MUG (4-methylumbelliferyl-β-D-glucoside) or X-glu (5-bromo-4-chloro-3-indolyl-λ-D-glucopyranoside). This will also determine whether other smaller active enzyme fragments are formed and their relative sizes.

C. Characterization of the Adsorption Properties of the Fusion Enzyme

Adsorption of cellulase to cellulose is presumed to be the first step required in the hydrolysis of insoluble cellulosic substrates. Enzyme binding to cellulose has been investigated for a few microbial cellulases with the aim of understanding how factors like enzyme concentration, enzyme, combination and ratio, temperature, pH and ionic strength of buffer might affect the adsorption kinetics of cellulase and the rate of cellulose degradation (Ghose & Bisaria, 1979; Moloney & Coughlan, 1983; Ooshima et al., 1983; Ryu et al., 1984; Andrease et al., 1987; Willaimson & Stutzenberge, 1987).

The ability of the fusion enzyme to bind to cellulosic substrate is analyzed by calculation of the adsorption equilibrium constant ($K_a$). Previous studies have shown that the adsorption of cellulase to cellulose follows the Langmuir isotherm equation (Langmuir, 1916):

$$C_b = \frac{C_{max} K_a C_f}{1 + K_a C_f} \quad (1)$$

where $C_b$ is the amount of enzyme bound per unit weight of cellulose at equilibrium, $C_f$ is the free enzyme concentration, $C_{max}$ is the maximum adsorption amount of enzyme and $K_a$ is the adsorption equilibrium constant. From equation (1), a more useful equation (2) is derived which can be plotted easily to obtain the values of $K_a$ and $C_{max}$. This is given as:

$$\frac{C_f}{C_b} = \frac{C_f}{C_{max}} + \frac{1}{K_a C_{max}} \quad (2)$$

Equation (2) is used to plot $C_f/C_b$ against $C_f$ to obtain a straight line according to the equation $y = mx + b$. The slope (m) is given by $1/C_{max}$ and the intercept (b) is given by $1/K_aC_{max}$. The values obtained for $K_a$ and $C_{max}$ are important in that they measure the adsorption affinity of the enzyme to the substrate and the number of adsorption sites per unit surface of the adsorbent, respectively. The $K_a$ value in particular is needed so that meaningful comparisons of the effects of different physical and chemical parameters on the adsorption of the fusion enzyme to cellulose can be made.

The ability of the enzyme to bind to Avicel is expressed as the percentage enzyme bound relative to the known activity concentration of the enzyme introduced into the system, of the free enzyme present in the supernatant fluid and of the bound enzyme eluted from substrate with distilled water. Kinetic studies on the adsorption process of the enzyme towards cellulosic substrate at varying enzyme concentration includes the determination of $K_a$ at different pH, temperature and ionic strength of the buffer. Stability (operational and storage) of the immobilized fusion protein is determined by binding the enzyme to Avicel in batch or column and allowing enzymatic reaction to occur as a function of time. The amount of glucose recovered, the activity concentration of the fusion protein and the amount of protein in the eluent versus time will indicate the stability of the immobilization scheme.

EXAMPLE 4

Isolation of DNA Fragment Responsible for Substrate Binding

To define the specific SBD peptide involved in substrate binding, several genetic approaches are available. One method uses restriction enzymes to remove a portion of the gene and then to fuse the remaining gene-vector fragment in-frame to obtain a mutated gene that encodes a protein truncated for a particular gene fragment. Another method involves the use of exonucleases (e.g., Bal31) to systematically 1 delete nucleotides either externally from the 5' and the 3' ends of the DNA or internally from a restricted gap within the gene. These gene deletion methods have the ultimate goal of producing a mutated gene encoding a shortened protein molecule, whose function may or may not be the same as the original protein molecule. Alteration of function in the truncated protein may be as a result of either the removal of that particular peptide fragment per se or from conformational changes in the modified protein as a result of deletion of some amino acids.

A. Deletion Using XmaIII Restriction Enzyme

Figure 6:
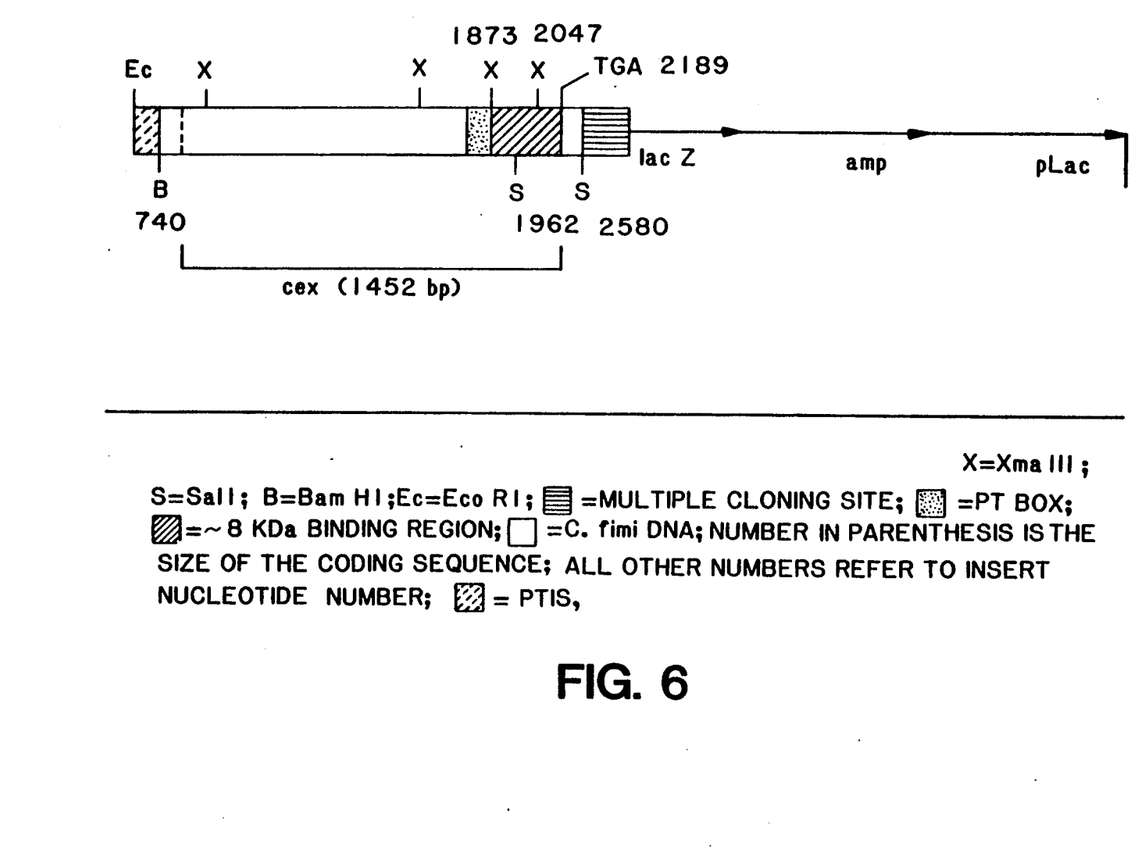
FIG. 6 is a schematic diagram of linearized pUC12-1.1cex (PTIS) showing relevant restriction sites.
Figure 7:
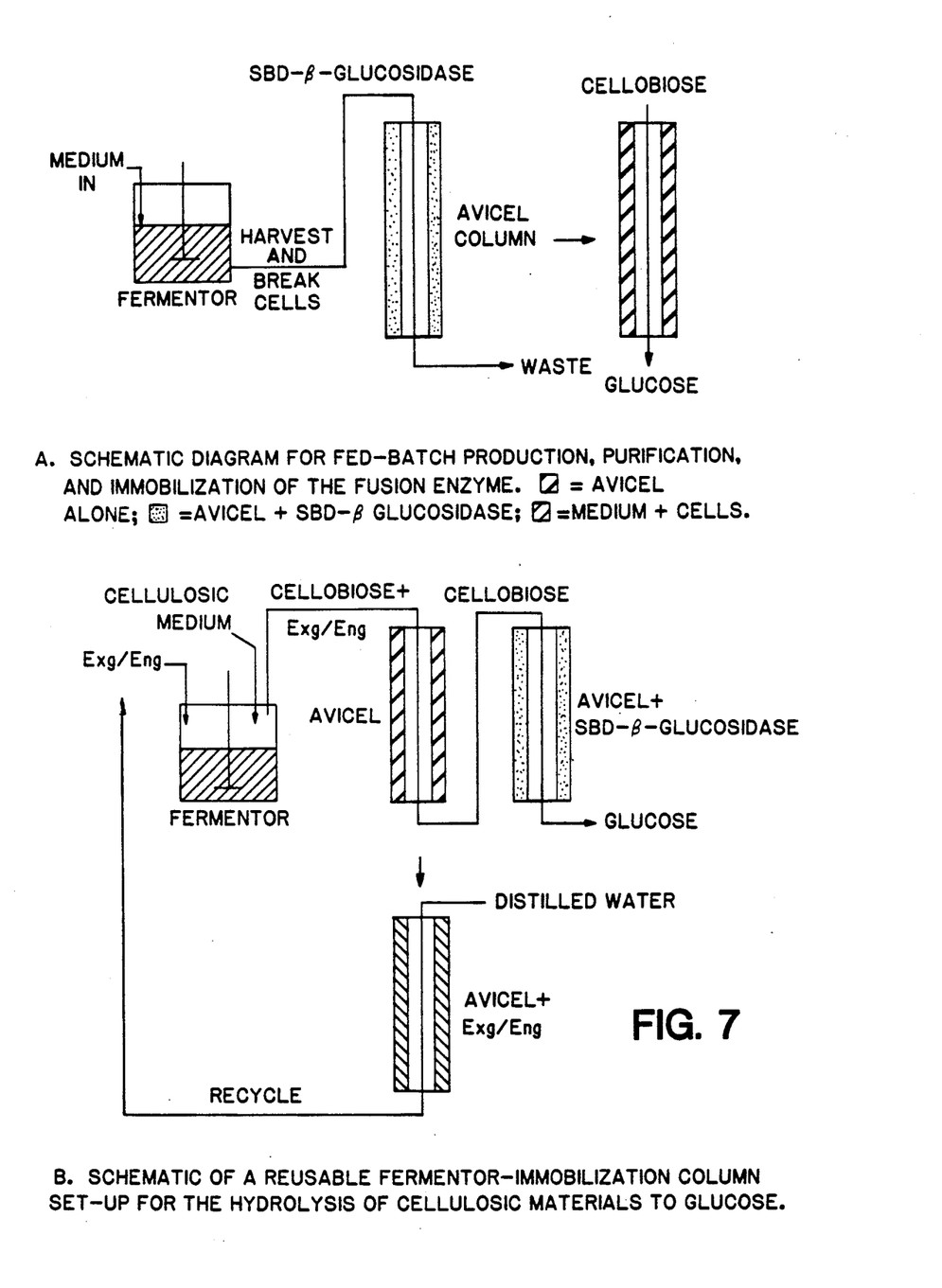
FIG. 7 is a schematic diagram of a reusable fermentor-immobilization column set up for the hydrolysis of cellulosic materials to glucose.
Figure 51:
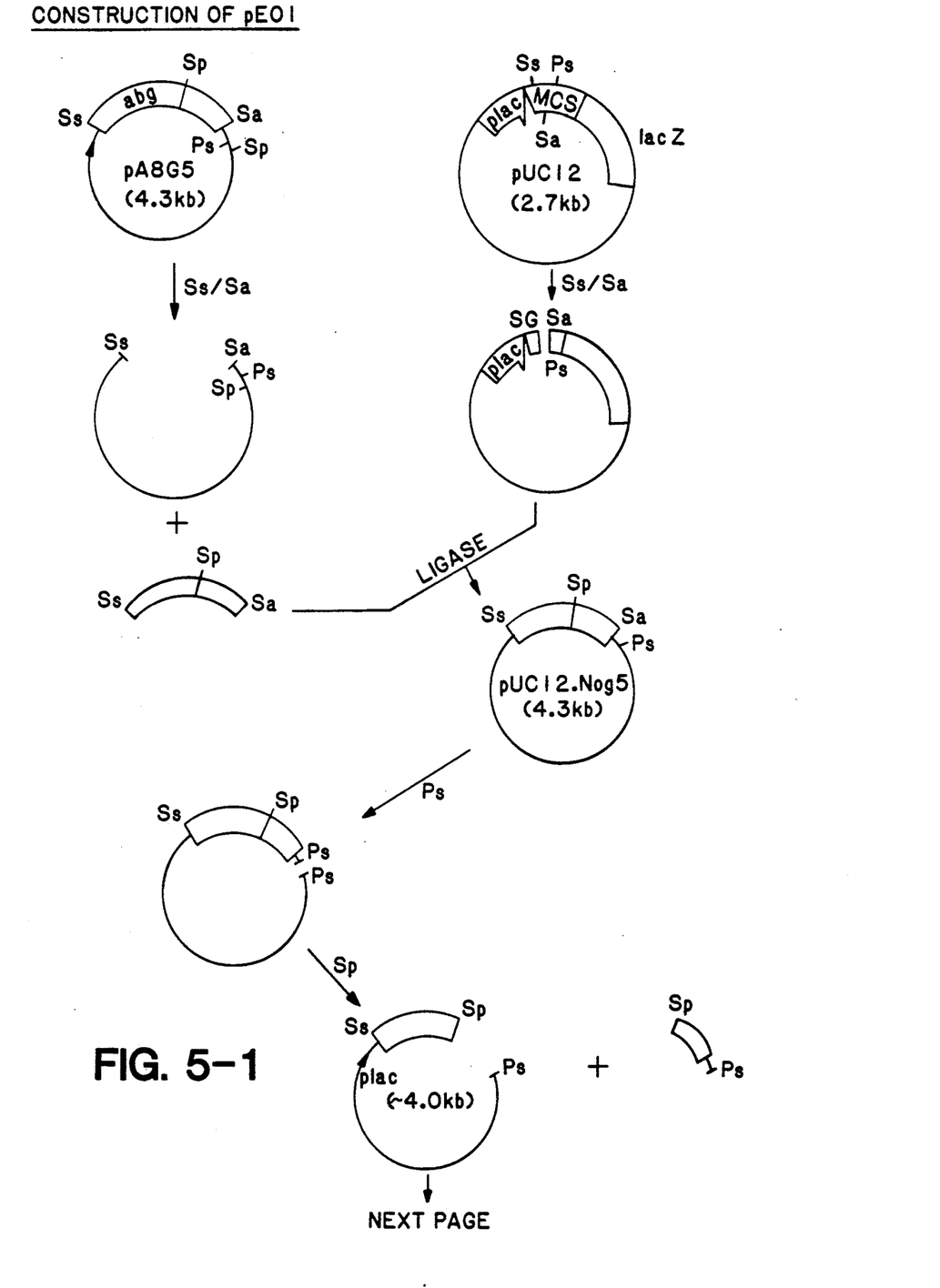
Figure 52:
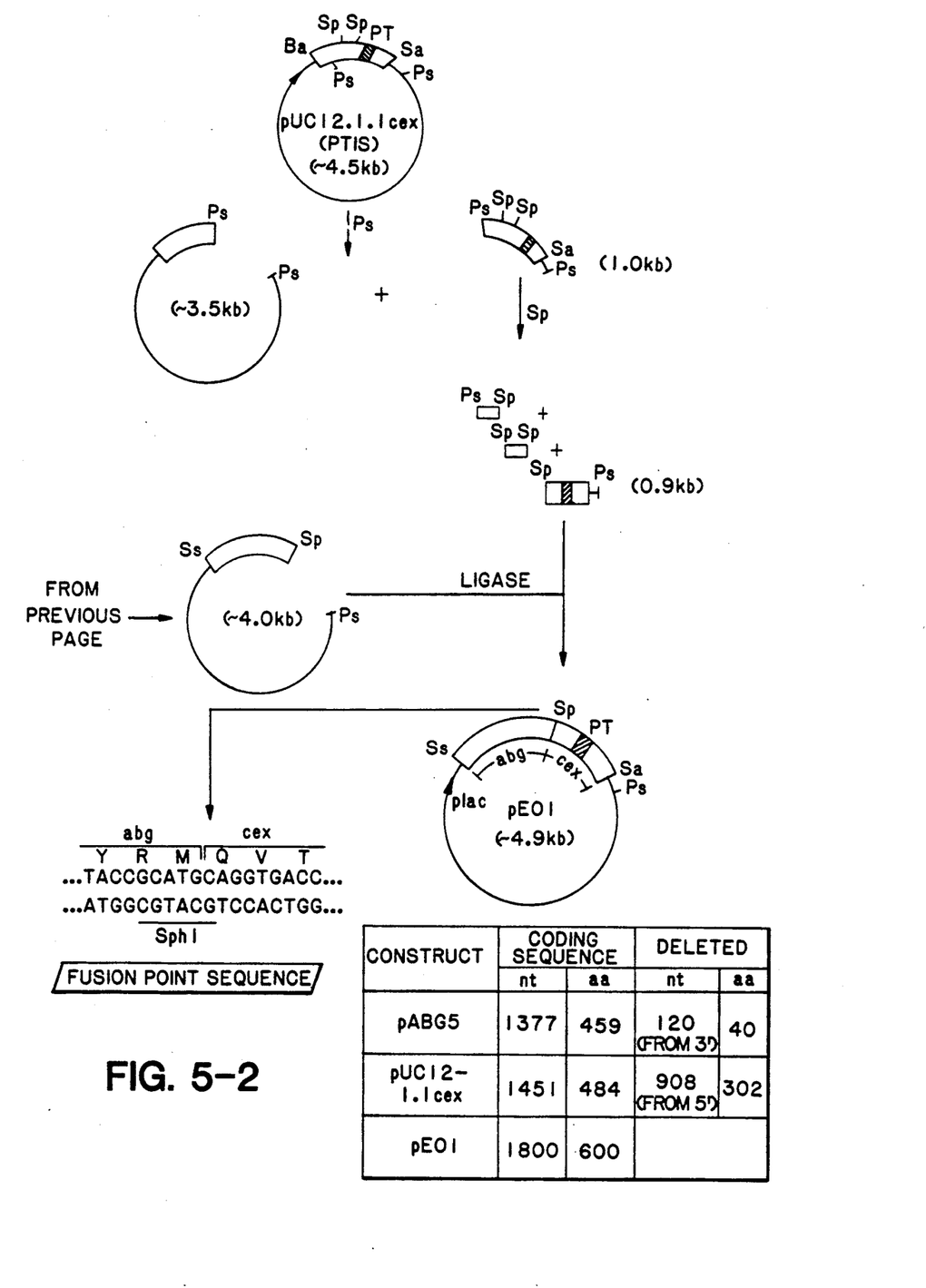

The plasmid pUC12-1.1cex (PTIS) is shown by FIG. 6 with the relevant restriction sites and sizes.

Initial binding studies of a SalI (S) partial digest of the plasmid eliminating that portion of the gene between nucleotide (nt) 1962 and nt 2580 have shown that the resulting truncated protein did not bind to Avicel. This result does not prove that the peptide encoded between the SalI site (nt 1962) to the stop codon (TGA at nt 2189) is the essential region for binding of the enzyme. The region just before the start of the deletion could have well been an important region for binding to cellulose. Another factor that could have contributed to the nonbinding to cellulose by the SalI deletion mutant is the formation of a fusion protein between the deleted Cex and the β-galactosidase of the vector.

Assuming an amino acid has an average molecular weight of 110, the deleted peptide in the SalI mutant is approximately 8 kD in size. This predicted size corresponds well to the size of a peptide that was purified by FPLC (Pharmacia) from a sample of proteolytically cleaved exoglucanase and that was subsequently found to bind tightly to Avicel. This result strongly suggests that the specific SBD peptide is within this apparent 8 kD region. The N-terminus of the FPLC purified approximate 8 kD peptide has been sequenced to determine exactly where the proteinase cleavage site is. Results indicate that the amino acid cleavage site occurs at the end of the PT box (between the last threonine and serine). Based on this amino acid sequence result, the calculated size of the SBD peptide should have been 11.3 kD. This discrepancy between the size of the FPLC purified SBD peptide and the calculated size as predicted from the amino acid cleavage site could have arisen from an aberrant migration of the peptide on the polyacrylamide gel.

To delineate further the amino acid sequence involved in substrate binding, the plasmid pUC12-1.1cex is digested partially with XmaIII (see Table 3). The linearized fragment corresponding to 5107 bp in size is isolated, religated and transformed into E. coli JM101. The gene portion between nt 1873 and nt 2074 is deleted and the remaining gene-vector is fused back together in-frame. The truncated protein produced and its binding affinity for Avicel is characterized and compared to the original cex protein.

B. Deletion Using Bal31

Bal31 is a highly specific nuclease that simultaneously degrades both the 3' and 5' ends of dsDNA without internal single-stranded cuts. Since there is an absolute requirement of the enzyme for $Ca^{++}$, the extent of deletion by the enzyme can be monitored and controlled by simply adding a divalent chelating agent, EGTA to the reaction mixture (Maniatis et al., 1982).

Before submitting the cex gene to Bal31 digestion, a loopout fragment containing the following regions is synthesized: 1) a restriction site where deletion will start (XbaI which is only found in the vector and just a few nucleotides downstream of the C. fimi gene insert); 2) a second restriction site not found in either the vector or the insert (NcoI); 3) a stretch of nucleotides containing stop codons in all three reading frames.

The loopout fragment is first annealed to a M13 ssDNA template containing the insert. The fragment is extended by adding d(A,T,G and C)TPs, Klenow polymerase and ligase. This fragment is transformed into E coli JM101 and the plaques hybridizing with the labeled loopout primer are picked up. The replicative form of DNA is isolated from the E. coli transformants. The duplex DNA is first cut with XbaI to linearize DNA. The same linearized DNA is then cut with NcoI. A stuffer DNA fragment containing C. fimi DNA flanked at one end with an NcoI site is also cut with NcoI. The stuffer DNA is ligated to the linearized DNA to regenerate an NcoI site. This construct is then digested with Bal31 which will digest from both ends (in the stuffer DNA and in the cex gene insert) at almost the same rate. The reaction mix is stopped periodically by removing a portion of the reaction sample and putting it into DNA buffer containing EGTA to stop Bal31 digestion. The stuffer DNA is removed by adding NcoI to the inactivated Bal31-digested DNA mixture. The DNA is then filled in with Klenow polymerase, size fractionated in an agarose gel and bluntligated to pUC12 to obtain a closed, circular, duplex DNA. A few microliters from the ligated mix is then cut with two restriction enzymes in such a way that small differences in the insert length as a result of deletion by Bal31 can easily be ascertained.

The DNA is transformed into competent *E. coli* JM101 cells. To screen for a family of mutants deleted at the 3' end of cex, antibody raised against the apparent 8 kD SBD peptide is used to identify positive deletion clones.

Truncated proteins produced from the different deletion mutants are tested for their ability to bind to Avicel and for their catalytic activity as described above.

EXAMPLE 5

Production of Glucose from Cellobiose Using β-glucosidase Fusion Protein Immobilized on Avicel This procedure uses endoglucanase-exoglucanase co-incubation with subsequent channeling of the resulting cellobiose mixture into an Avicel column immobilized with β-glucosidase. The method is as follows. In a fermentation vessel, a suitable proportion of both endoglucanase and exoglucanase is added to a medium containing the cellulosic material to be degraded. The enzymes are allowed to react for a fixed period of time to produce cellobiose, which is solubilized in the medium. The whole spent medium together with the enzyme is first passed through an Avicel column which will immobilize and concentrate both the endoglucanase and the exoglucanase. The eluent containing the cellobiose is channeled to a second column immobilized with β-glucosidase fusion protein which then hydrolyzes the cellobiose into glucose units. The endoglucanase and the exoglucanase are regenerated from the first column by simply eluting them out with distilled water. Both columns can be reused several times for purification and enzymatic conversion.

EXAMPLE 6

Preparation of cenA-alkaline Phosphatase Fusion Protein Expression Cassette

TnphoA is a derivative of transposon Tn5 containing the *E. coli* alkaline phosphatase gene, phoA, minus its signal sequence ('phoA). Transpositional insertion into an expressed gene in the correct reading frame creates a PhoA fusion protein. If the target gene contains protein export signals, these can direct the secretion of the fusion protein. This secretion is detectable by alkaline phosphatase activity, which is present only when the enzyme has a periplasmic location. TnphoA is used to create phoA gene fusions with the *C. fimi* cenA gene in a plasmid having a multiple cloning site. A gene encoding a protein of interest can be cloned into the multiple cloning site and expressed as a fusion protein. The gene product is purified by binding to cellulose, such as Avicel, and cleavage from the CenA fusion partner with *C. fimi* protease A. Preparation and Analysis of Gene Fusions Transpositional mutagenesis with TnphoA is used to create gene fusions with cenA. The plasmid containing cenA is pUCEC2, a 1.6 kb SstI cenA fragment cloned in pTZ18U, a multifunctional derivative of pUC18 (Yanisch-Perron et al., Gene (1985) 33:103-119). pTZ18U is available from U.S. Biochemicals.

Oligonucleotide-directed matagenesis (Zoller et al., *Nucleic Acids Res.* (1982) 10:6487-6500 and Zoller et al., *Methods Enzymol.* (1983) 100:468-500) was used to delete the carboxy-terminal portion of the cenA gene and juxtapose the Pro-Thr box and the multiple cloning site of pTZ18U. Screening procedures include dot blot hybridization using the mutagenic oligonucleotide as a probe, and restriction analysis. DNA sequencing by the chain-termination method was performed to verify the sequence of the deletion region (Yanisch-Perron, supra).

The transposition event was mediated by infection of *E. coli* CC118 (pUCEC2) with a defective lambda phage containing the transposon, λTnphoA-1 (Gutierrez et al., *J. Mol. Biol.* (1987) 195:289-297). *E. coli* CC118 contains a deletion in the phoA gene. Transpositional insertion into the cenA gene in-frame with CenA the periplasm, secretion being promoted by the CenA signal peptide. Colonies selected for kanamycin (transposon-derived) and ampicillin resistance were screened for alkaline phosphatase activity on the indigogenic substrate 5-bromo-4-chloro-3-indolyl phosphate (XP). Plasmid DNA from PhoA+ colonies was retransformed, and selected and screened as above. PhoA+ colonies were screened for endoglucanase activity on carboxymethylcellulose (CMC) plates stained with Congo red (Gilkes et al., *Bio/Technology* (1984) 2:259-263). The desired penotype is PhoA+, Eng-, and resistance to ampicillin and kanamycin.

Plasmid DNA was isolated from PhoA+, EngA- colonies and analyzed by restriction digestion and agarose gel electrophoresis. Of 55 colonies screened, 34 had TnphoA insertions in cenA in the correct orientation. The insertions occurred throughout the cenA gene. Some of these clones may have out-of-frame insertions, a possibility that will become evident when looking at the protein products of the fusions. Analysis of cellulose binding of some of the CenA-PhoA fusion proteins shows that the fusion proteins bind to filter paper, despite stringent washes with 50 mM phosphate buffer (pH 7.0) and 0.5 M NaCl.

One fusion protein which binds to cellulose is selected for further study. The exact insertion position of TnphoA is determined by DNA sequencing using the chain-termination method. The buffer conditions which facilitate binding to Avicel and for which elution from Avicel occurs are also determined as described above (see Example 3).

The Avicel-bound fusion protein is incubated with *C. fimi* protease, and released proteolytic fragments are concentrated by ultrafiltration and analyzed by SDS-PAGE and PhoA activity zymogram or Western immunoblot, or by gel filtration chromatography. Substrate-bound fragments are dissolved in SDS and analyzed by SDS-PAGE and Western immunoblot, probed with antiserum to the Pro-Thr box (Langsford et al., *FEBS Letters* (1987) 225:163-167).

B. Purification of Fusion Protein

Cleared *E. coli* cell extracts containing the fusion protein are applied to an Avicel column in a buffer which promotes binding of the fusion protein to the Avicel matrix. After thorough washing of the column with buffer to remove non-specifically bound proteins, *C. fimi* protease is applied to the column and washed through with buffer. Collected fractions are assayed for alkaline phosphatase activity, and the enzyme peak further purified by ion exchange or gel filtration chromatography. Purification conditions, such as protease concentration and flowrate, are varied to optimize the recovery of alkaline phosphatase activity.

EXAMPLE 7

Use of Cellulomonas fimi Cellulose Binding Domains for Drug Delivery

A. Solubility/Persistence Interleukin 2

A fusion protein comprising interleukin 2 (IL-2) linked to the cellulose binding region of a *C. fimi* cellulase is prepared as described above by preparing a fusion gene comprising at least the DNA sequence encoding the CenA or Cex cellulose binding region and a gene encoding IL-2 or a functional portion thereof and transforming it into an expression host such as *E. coli*. The fusion protein is purified by affinity chromatography on cellulose (Avicel or cotton). The fusion protein is eluted with water and then bound to soluble (carboxymethyl) or insoluble (Avicel) cellulose. These conjugates are injected into mice (i.p.) and the kinetics of IL-2 clearance from the peritoneal fluid determined. The soluble conjugate is injected i.v. and the kinetics of clearance of IL-2 activity from the blood determined. The conjugates find use in decreasing the clearance rate of IL-2 from the circulation.

B. Antigenicity/Adjuvant Activity

Two fusion proteins comprising IL-2 and alkaline phosphatase respectively linked to the cellulose binding region of *C. fimi* cellulase, prepared as described above, are bound to the same cellulose preparation through the cellulose binding region on each fusion protein. Both soluble (for example, carboxymethyl) and insoluble (for example, Avicel) cellulose matrices are used. The combined matrix IL-2-CBR→cellulose←CBR-alkaline phosphatase is injected into mice and the immune responses (T-cell proliferation and anti-alkaline phosphatase antibody concentration) determined after 1 week and 2 weeks. These responses are compared to the response generated by injecting an identical amount of alkaline phosphatase-CBR. In subsequent experiments HIV gp 120-CBR and *Pseudomonas porin*-CBR are tested in an analogous system replacing alkaline phosphatase. The combination of IL-2 in close proximity to an antigen finds use in enhancing the immune response to the presented antigen.

The compositions of the subject invention comprise hybrid proteins in which at least the polysaccharide binding domain of a polysaccharidase is fused to a polypeptide of interest. The compositions find use for binding a variety of ligands to a polysaccharide matrix, either soluble or insoluble. They may be used bound to the matrix, for example as drug delivery systems, or in fermentors, or they may be used as a means of isolating or purifying the ligand, then recovering the ligand following cleavage with a specific protease.

All publications and patent applications mentioned in this specification are indicative of the i level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method using an affinity matrix for immobilization of a polypeptide of interest, the improvement which comprises:

preparing a fusion protein comprising said polypeptide of interest and an amino acid sequence comprising a substrate binding region of a cellulose with the provisio that said amino acid sequence is essentially lacking in cellulose activity; and contacting said fusion protein with an affinity matrix comprising a cellulose substrate for said cellulose whereby said substrate binding region binds to said affinity matrix.

2. A method according to claim 1, wherein said polypeptide of interest is a $\beta$-glucosidase or interleukin-2.

3. In a method using an affinity matrix for purification of a polypeptide of interest, the improvement which comprises:

preparing a fusion protein comprising said polypeptide of interest and an amino acid sequence comprising a substrate binding region of a cellulose, with the proviso that said amino acid sequence is essentially lacing in cellulose activity;

contacting said fusion protein with an affinity matrix comprising a cellulose substrate for said cellulose whereby said substrate binding region binds to said affinity matrix; and separating the fusion protein or the polypeptide of interest from the affinity matrix.

4. The method according to claim 3, wherein said substrate binding region is contained by cellulase is obtained from *Cellulomonas fimi*.

5. The method according to claim 4, wherein said substrate binding region is contained by cellulase obtained from *Cellulomonas fimi*.

6. The method according to claim 3, wherein said affinity matrix is microcrystalline cellulose.

7. The method according to claim 3, wherein said polypeptide of interest is an alkaline phosphatase.

* * * * *

UNITED STATES PATENT AND TRADEMARK OFFICE
CERTIFICATE OF CORRECTION

PATENT NO. : 5,137,819

DATED : August 11, 1992

INVENTOR(S) : Douglas Kilburn

It is certified that error appears in the above-indentified patent and that said Letters Patent is hereby corrected as shown below:

In column 8, line 10, replace "below in Table 1" with -- in FIG. 2--.
In column 12, line 18, replace "Table 3" with -- FIG. 6 --.
In column 15, line 49, replace "the i level" with -- the level --.
In Column 16, Claim 4, line 2, delete "is". (second occurrence).

Signed and Sealed this

Nineteenth Day of October, 1993

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. :    5,137,819
ISSUE DATE :    August 11, 1992
INVENTOR(S):    D. Kilburn, R. Miller, R. Warren and N. Gilkes
TITLE :         CELLULOSE BINDING FUSION PROTEINS FOR IMMOBILIZATION AND PURIFICATION OF POLYPEPTIDES

It is certified that error appears in the above-identified patent and that said Letters Patent is hereby corrected as shown below:

In column 1, line 26, after "β-galactosidase" insert --can--.

In column 2, line 23, "cex and cenA" should read --*cex and cenA*--;

And in line 37, "C. fimi" should read --*C. fimi*--.

In column 16, line 17, "cellulose" should read --cellulase--;

In line 19, "cellulose" should read --cellulase--;

In line 21, "for said cellulose" should read --for said cellulase--;

In line 31, "cellulose" should read --cellulase--;

In line 33, "lacing in cellulose" should read --lacking in cellulase--;

In line 35, "cellulose" (second occurrence) should read --cellulase--;

Signed and Sealed this

Eleventh Day of April, 2000

Attest:

Q. TODD DICKINSON

Attesting Officer

Director of Patents and Trademarks